(12) United States Patent
Eggersmann

(10) Patent No.: US 9,096,822 B2
(45) Date of Patent: *Aug. 4, 2015

(54) DEVICE TO PRODUCE BIOGAS

(75) Inventor: Karlgünter Eggersmann, Marienfeld (DE)

(73) Assignee: Zero Waste Energy, LLC., Lafayette, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 13/352,702

(22) Filed: Jan. 18, 2012

(65) Prior Publication Data

US 2013/0183752 A1    Jul. 18, 2013

(51) Int. Cl.
| | | |
|---|---|---|
| C12M 1/00 | (2006.01) | |
| C12M 3/00 | (2006.01) | |
| C12M 1/107 | (2006.01) | |
| C12M 1/16 | (2006.01) | |

(52) U.S. Cl.
CPC ............... *C12M 21/04* (2013.01); *C12M 21/16* (2013.01); *C12M 29/02* (2013.01); *Y02E 50/343* (2013.01)

(58) Field of Classification Search
CPC ....... C12M 21/04; C12M 21/16; C12M 23/40
See application file for complete search history.

(56) References Cited

U.S. PATENT DOCUMENTS

| | | | | |
|---|---|---|---|---|
| 6,110,727 | A * | 8/2000 | Widmer et al. | 435/262 |
| 6,699,708 | B1 * | 3/2004 | Muller et al. | 435/262 |
| 7,854,840 | B2 * | 12/2010 | Busch et al. | 210/603 |
| 2007/0259416 | A1 * | 11/2007 | Parker et al. | 435/266 |
| 2009/0068725 | A1 * | 3/2009 | Lutz | 435/286.5 |

FOREIGN PATENT DOCUMENTS

| | | |
|---|---|---|
| DE | 202006002757 | 8/2007 |
| EP | 1428868 | 6/2004 |
| EP | 1736535 | 12/2006 |
| EP | 2275525 | 1/2011 |
| WO | 0206439 | 1/2002 |

* cited by examiner

*Primary Examiner* — Nathan Bowers

(57) ABSTRACT

A device to produce biogas that includes at least one fermenter (1) to receive a substrate (2) to be percolated, and a percolate container (3). The fermenter (1) and the percolate container (3) are connected with each other such that the percolate within the fermenter (1) seeping through the substrate (2) makes its way into the percolate container (3) which serves as a thermal reservoir, from which it may be directed back to the fermenter (1) as necessary. The percolate container (3) serving as a thermal reservoir and/or the sand trap which serves as a percolate collector (5) are located at least partially below the floor surface (1a) of the fermenter (1).

11 Claims, 3 Drawing Sheets

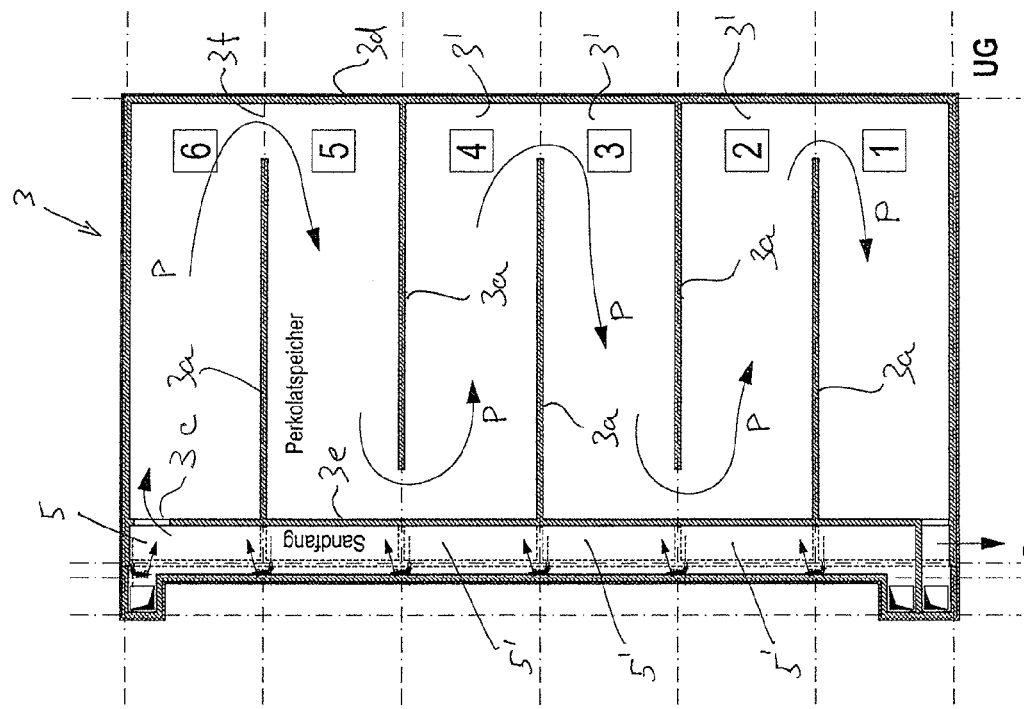
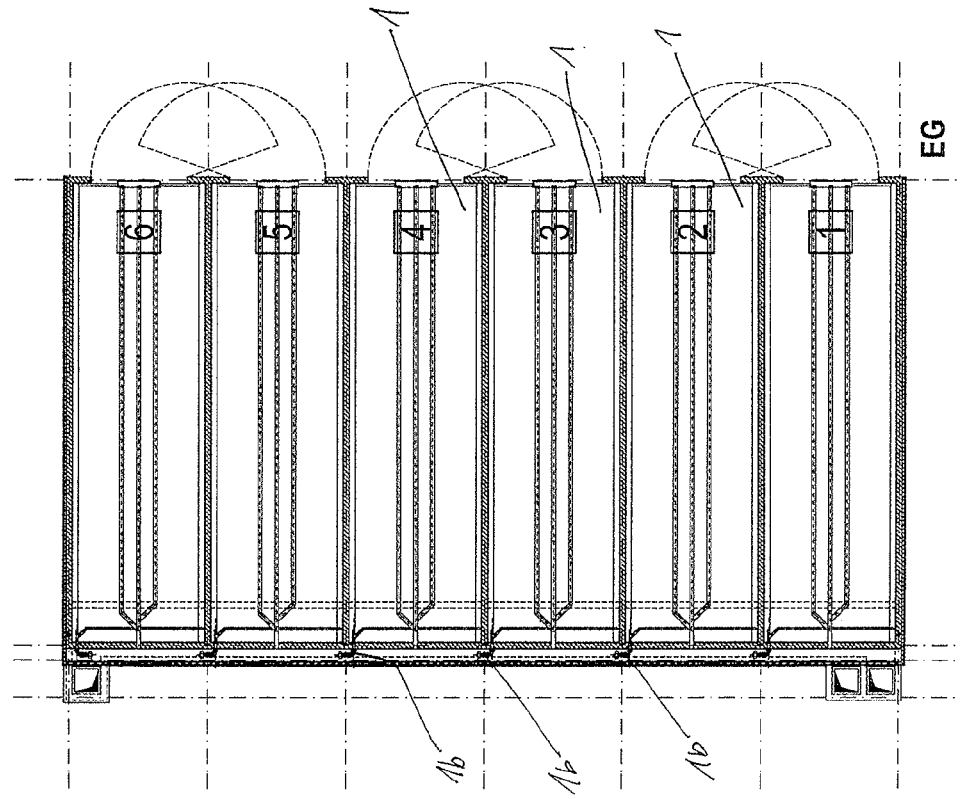

DEVICE TO PRODUCE BIOGAS

TECHNICAL FIELD

The invention relates to a device to produce biogas and more particularly, to a device wherein the percolate container may be used for thermal conditioning of the substrate and wherein by virtue of its design the creation of synergistic effects, which lead to a more compact and energy-saving design for fermenter systems, leading to modular configurations of such systems.

BACKGROUND INFORMATION

In biogas systems that particularly use the principle of dry fermentation, biomass is fermented within a box-shaped fermenter by means of percolation with a percolate such that biogas is produced. During this, the percolate as a rule is trapped and transferred into an external percolate container, from which the percolate in turn is recycled to the fermenter.

During this, it is important that the temperature of the substrate and/or of the percolate does not drop too much, since otherwise fermentation is inhibited. In known systems, however, heat loss plays a significant role.

To solve this problem, one may deal with heating of the percolate within the percolate tank, or with heating the substrate within the fermenter.

Both approaches require the provision of energy, such that conventional means are lacking in energy efficiency.

SUMMARY

It is therefore one object of the invention to provide a device of the type mentioned at the outset in which these disadvantages are reduced, and that will operate more efficiently regarding energy consumption.

According to the teachings of the invention, a percolate collector and/or thermal reservoir are positioned beyond the floor surface of at least one fermenter. The percolate container advantageously serves as the thermal reservoir. Positioning the percolate collector and/or percolate container near the fermentation, allows practical dispensation of tubing lines to connect the sand trap, fermenter, and percolate container, so that a former source of heat loss is eliminated. Additionally, the percolate collector and particularly the percolate container may serve as thermal reservoirs. The percolate passing from the fermenter into the percolate container during the process serves as a heat source, and as heating for the substrate located within the percolate. Heating may advantageously be provided within the percolate container to heat the percolate.

The percolate collector is configured as a sand trap and/or collection line for streams of percolate.

According to a particularly advantageous embodiment, the system has a modular structure in which each module consists of a sand trap section and/or a percolate container section. The modules are advantageously box-shaped so that they may be positioned adjacent to one another, thus combining the sand trap section and/or a percolate container section into one sand trap and/or percolate container. The percolate container thus has an inlet and an outlet, and advantageously includes wall sections between inlet and outlet positioned such that the percolate in the percolate container is fed meanderingly from inlet and outlet, thus ensuring constant mixing of the percolate.

BRIEF DESCRIPTION OF THE DRAWINGS

These and other features and advantages of the present invention will be better understood by reading the following detailed description, taken together with the drawings wherein:

FIG. 3A illustrates the layout of the first layer of a device based on the invention with multiple fermenters and FIG. 3B illustrates the layer below the first layer of a device based on the invention with multiple fermenters.

Figure 1:
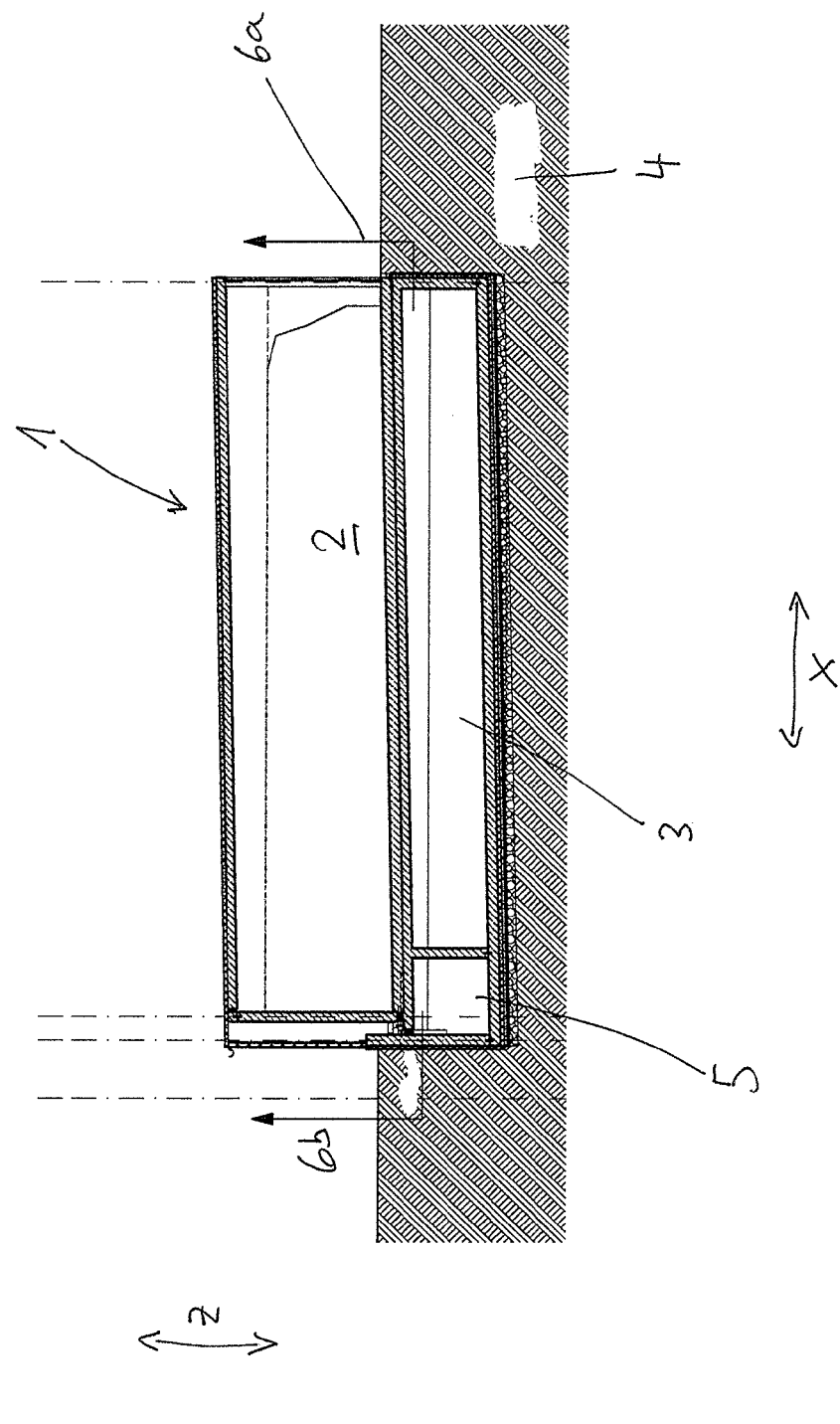
FIG. 1 is a cutaway view through a device based on the invention.

In the following, the term sand trap will be used figuratively. This is merely a special configuration of a percolate collector. Alternatively, the following description also applies to a collecting line or other particulate-matter separator or similar. The cutaway view in FIG. 1 shows a fermenter 1, here configured as a box fermenter and positioned at the floor level in order to be supplied via a wheel loader with substrate 2 to be fermented. The fermenter 1 includes a floor 1a on which the substrate 2 rests. First, a sand trap 5 is positioned below the floor section 1a near the face end of the fermenter 1. A percolate container 3 is adjacent to the sand trap 5 below the floor section 1a. Both sand trap 5 and percolate container 3 possess biogas outlets to extract the biogas being produced there via lines 6b and 6a. The fermenter 1 also possesses corresponding outlets (not shown). Sand trap 5 and percolate container 3 are at least partially embedded into the base 4 so that waste heat arising there is not predominantly lost to the atmosphere. The floor surface 1a of the fermenter 1 is inclined, in the illustrated example, the floor surface 1a upon which the substrate 2 rests slopes down toward the end of the fermenter 1, in whose vicinity the sand trap 5 is positioned. Thus, the percolate seeping through the substrate 2 during the process flows along the floor 1a of the fermenter 1 to the above-mentioned end, and may there be guided into the sand trap 5.

Figure 2:
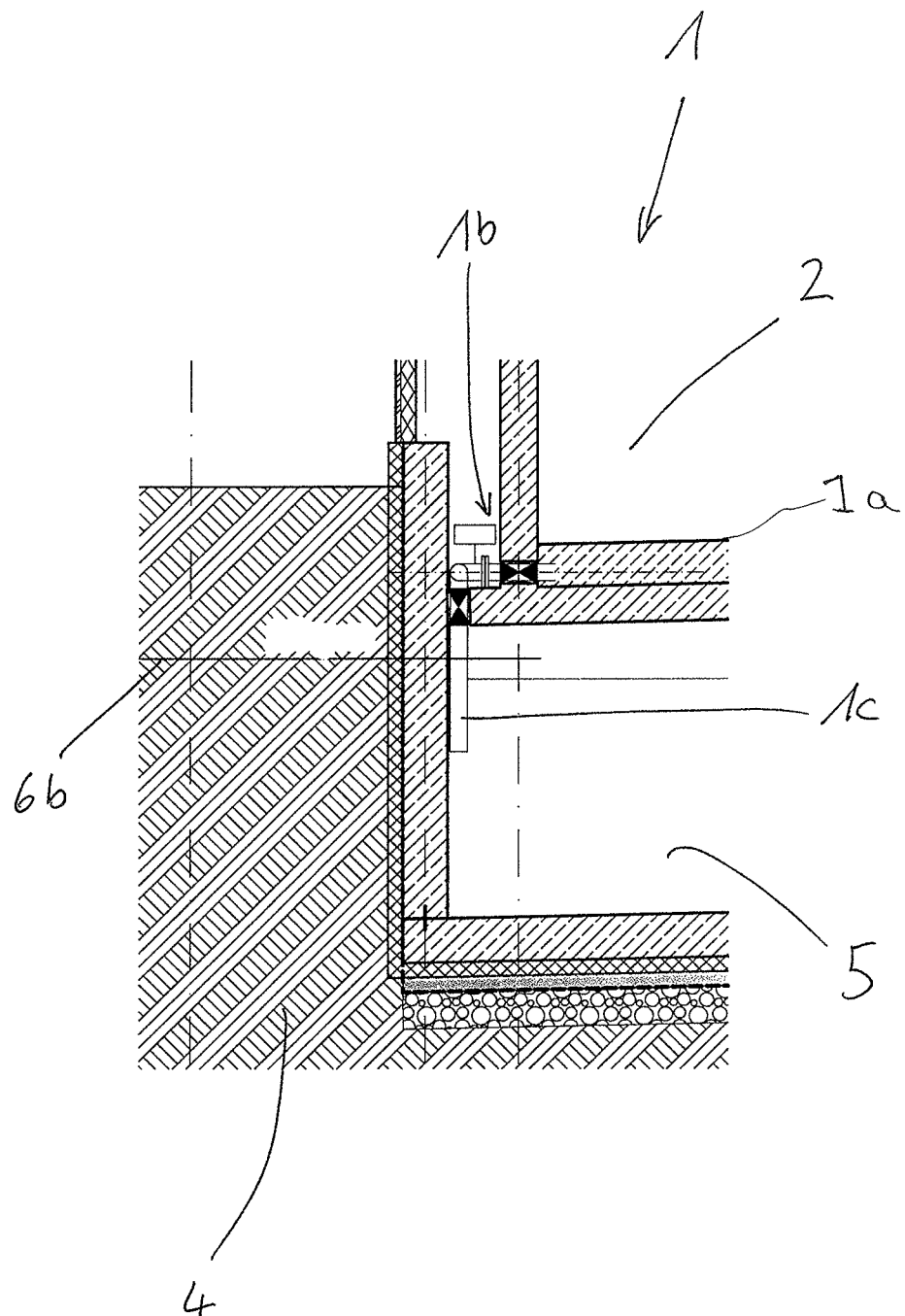
FIG. 2 is an enlarged sectional view from FIG. 1.

As FIG. 2 shows, a closeable outlet 1b is provided in the floor 1a at this end of the fermenter 1. This outlet leads via a short tubing line 1c into the sand trap 5 such that no gas may be exchanged via tubing line 1c. Line 1c, typically several meters long, which is between fermenter 1 and a sand trap 5 is reduced to a few centimeters by means of the configuration of the sand trap 5 based on the invention.

Further, a closeable connection (not shown) is provided between the sand trap 5 and percolate container 3 through which the percolate that is cleansed in the sand trap 5 flows to the percolate container 3, from which it may again be recycled through fermenter 1. As FIG. 1 shows, the percolate container 3 embedded in the base 4 extends over a significant portion of the length of the fermenter 1 so that a large heat-exchange surface is available between fermenter 1 and percolate container 3. The percolate container, and to a certain extent, the sand trap 5 with smaller surface area may be operated and used based on the invention as a heat reservoir to heat the substrate 2 within the fermenter 1. Heating of the percolate within the percolate container 3 may cause the heat-exchange surface to heat the substrate 2. Tubing lines to transport the percolate are hardly required.

Also, the invention allows a space-saving configuration when compared to conventional systems. On the one hand, this is enabled by the layered structure, and on the other, the structure may be modular such that the percolate container "grows with" the requirements of expanding systems.

FIGS. 3A and 3B show horizontal projections of such a system through the first level of fermenters 1 (base level, EG)

and the level below it consisting of sand trap 5 and percolate container 3 (lower level, UG), which in this example consists of six modules. In the longitudinal section, the EG essentially corresponds to the cutaway view in FIG. 1. Each fermenter 1 includes an outlet 1*b* through which the trapped percolate is fed to the sand trap 5 so that percolate flows into a pertinent sand trap section 5' below each fermenter 1. A percolate container section 3' is adjacent to each of the sand trap sections 5', which together form the sand trap 5, at whose end a closeable aperture 5*a* is provided. A module is thus formed by a fermenter 1 and a section of the sand trap 5' and a percolate container 3' positioned below it. The percolate containers 3' in turn form the percolate container 3 which includes an inlet 3*c* for connection with the outlet 5*a* of the sand trap 5 and an outlet 3*b* to extract the percolate, which in turn may be fed into the fermenter 1 again as necessary.

Advantageously, only one inlet 3*c* and the outlet 3*b* for the modularly-structured percolate container 3 are provided. It is further advantageously provided that the flow path within the percolate container between inlet and outlet is as long as possible. To this end, intermediary walls are provided within the percolate container 3 that essentially extend along the vertical dimension Z with longitudinal sides of the fermenter 1. These intermediary walls 3*a* extend advantageously along the longitudinal dimension X of the fermenter, crosswise to the dimension Y of the adjacent modules, and/or crosswise to the length of the modularly-structured sand trap 5. For this, these intermediary walls do not extend, however, across the entire length between two face sides 3*e*, 3*d* of the percolate container sections 3', but rather leave an open space toward a face side 3*e*, 3*d* so that the percolate (as the arrow P shows) may meander through the percolate container 3 between inlet 3*c* and outlet 3*b*. Thus, the comparative holding duration of the percolate is achieved so that particularly homogenous temperature distribution is ensured within the percolate.

This invention allows for at least two (2) advantages: First; the percolate container may be used for thermal conditioning of the substrate 2, and second, it causes through its design the creation of synergistic effects, which lead to a more compact and energy-saving design for fermenter systems, leading to modular configurations of such systems.

Modifications and substitutions by one of ordinary skill in the art are considered to be within the scope of the present invention, which is not to be limited except by the following claims.

The invention claimed is:

1. A device for fermenting a substrate and for obtaining biogas from said fermented substrate, said device having at least one fermenter (1) for receiving a substrate (2) which is to be percolated during fermentation, as well as a percolate container (3) for recovering percolate, wherein the fermenter (1) and percolate container (3) are fluidly connected to one another so that the percolate seeping through the substrate (2) disposed on one side of a generally non-porous base surface (1*a*) in the fermenter (1) passes into the percolate container (3) and can be returned from there when necessary back again into the fermenter (1), wherein at least in part on a second side of the generally non-porous base surface (1*a*) of the fermenter (1) there is a heat reservoir in the form of the percolate container (3) and a percolate collecting device (5), characterised in that the percolate collecting device (5) is fluidly connected between the fermenter (1) and the percolate container (3) and is arranged underneath the generally non-porous base surface (1*a*) of the fermenter (1) and laterally adjacent said percolate container (3) and configured for cleaning percolate flowing from the fermenter (1), such that percolate flowing from the fermenter (1) first flows into the percolate collecting device (5) to be cleaned prior to said cleaned percolate flowing into the percolate container (3), and wherein said generally non-porous base surface (1*a*) forms a common heat exchange surface between at least the percolate container (3) and the fermenter (1).

2. The device according to claim 1, characterised in that the percolate container (3) is provided underneath the fermenter (1) at least partially in the ground (4).

3. Device according to claim 1, characterised in that the fermenter (1) has a generally non-porous base surface (1*a*) which is formed inclined in at least some sections so that percolate seeping through the substrate (2) disposed in the fermenter (1) can flow along said generally non-porous base surface (1*a*) in the direction of a collection region in a wall and/or corner of the fermenter.

4. The device according to claim 3 characterised in that the fermenter (1) has at least one outlet (1*b*) in said collection region for letting out the percolate collected from said fermenter (1) and into said collecting device (5).

5. The device according to claim 1, characterised in that a number of fermenters (1) are provided which are arranged side by side and wherein a common percolate container (3) is provided disposed underneath said number of fermenters.

6. The device according to claim 5, characterised in that partitions (3*a*) are provided in the common percolate container (3) and are arranged so that percolate entering into the common percolate container (3) at inlet (3*c*) is guided meandering through the percolate container (3) between the percolate inlet (3*c*) and a percolate outlet (3*b*).

7. The device according to claim 6, characterised in that an outlet (1*b*) of each of the number of the fermenters (1) open into a common percolate collecting device (5) which extends along and under the number of fermenters (1) and has a collecting device outlet (5*a*) which opens into the percolate inlet (3*c*) of the percolate container (3).

8. The device according to claim 7, characterised in that the device includes a number of modules wherein at least two modules have a fermenter (1), a percolate collecting device section (5') and a percolate container section (3'), and wherein each fermenter (1) has an outlet (1*b*) opening into the associated percolate collecting device section (5') of the associated fermenter (1).

9. The device according to claim 1, characterised in that the percolate collecting device (5) is a sand trap.

10. The Device according to claim 1 wherein said percolate collecting device (5) and said percolate container (3) each include a biogas venting outlet (6*a*, 6*b*).

11. A device for fermenting a substrate and for obtaining biogas from said fermented substrate, said device having at least one fermenter (1) for receiving a substrate (2) which is to be percolated during fermentation, as well as a percolate container (3) for recovering percolate, wherein the fermenter (1) and percolate container (3) are fluidly connected to one another so that the percolate seeping through the substrate (2) disposed on one side of a generally non-porous base surface (1*a*) in the fermenter (1) passes into the percolate container (3) and can be returned from there when necessary back again into the fermenter (1), wherein at least in part on a second side of the base surface (1*a*) of the fermenter (1) there is a heat reservoir in the form of the percolate container (3) and a percolate collecting device (5), characterised in that the generally non-porous base surface (1*a*) of the fermenter (1) is formed inclined in at least some sections so that percolate seeping through the substrate (1) disposed in the fermenter (1) can flow along said generally non-porous base surface (1*a*) in the direction of a collection region in a wall and/or corner of the fermenter and wherein the fermenter (1) has at least one outlet (1b) in said collection region, for letting out the percolate collected from said fermenter (1) and into said collecting device (5), wherein the percolate collecting device (5) is a sand trap and is fluidly connected between the fermenter (1) and the percolate container (3) and is arranged underneath the base surface (1a) of the fermenter (1) and laterally adjacent said percolate container (3) and configured for cleaning percolate flowing from the fermenter (1), such that percolate flowing from the fermenter (1) first flows into the percolate collecting device (5) to be cleaned prior to said cleaned percolate flowing into the percolate container (3), and wherein said base surface (1a) forms a common heat exchange surface between at least the percolate container (3) and the fermenter (1).

* * * * *